United States Patent [19]

Chodnekar et al.

[11] 4,001,339
[45] Jan. 4, 1977

[54] PHENYL DERIVATIVES

[75] Inventors: Madhukar Subraya Chodnekar, Basel; Albert Pfiffner; Norbert Rigassi, both of Arlesheim; Ulrich Schwieter, Reinach; Milos Suchy, Basel, all of Switzerland

[73] Assignee: Hoffmann-La Roche Inc., Nutley, N.J.

[22] Filed: Jan. 17, 1975

[21] Appl. No.: 541,749

Related U.S. Application Data

[60] Division of Ser. No. 279,897, Aug. 11, 1972, Pat. No. 3,879,429, which is a continuation-in-part of Ser. No. 30,295, April 20, 1970, Pat. No. 3,944,531.

[30] Foreign Application Priority Data

| Apr. 30, 1969 | Switzerland | 6597/69 |
|---|---|---|
| Mar. 23, 1970 | South Africa | 70/2003 |
| Apr. 7, 1970 | Australia | 13535/70 |

[52] U.S. Cl. .................. 260/612 D; 260/240 R; 260/327 E; 260/340.3; 260/340.7; 260/348 A; 260/348 R; 260/465 F; 260/479 C; 260/592; 260/599; 260/600 R; 260/609 R; 260/611 A; 260/613 D; 260/613 R; 424/275; 424/278; 424/300; 424/304; 424/331; 424/337; 424/340; 424/341

[51] Int. Cl.$^2$ ............................ C07C 43/20
[58] Field of Search ............... 260/612 D; 424/340

[56] References Cited

UNITED STATES PATENTS

| 3,711,519 | 1/1973 | Dolejs et al. | 260/348 R |
|---|---|---|---|
| 3,732,254 | 5/1973 | Siddall | 260/612 D |
| 3,825,602 | 7/1974 | Pallos et al. | 260/612 D |

OTHER PUBLICATIONS

Snell et al., "Annual Review of Biochemistry," (1971), pp. 1079, 1096, 1097.

*Primary Examiner*—V. D. Turner
*Attorney, Agent, or Firm*—Samuel L. Welt; Bernard S. Leon; William H. Epstein

[57] ABSTRACT

Phenyloxy, phenylsulfinyl, phenylthio, phenylsulfonyl, benzyloxy, benzylthio, benzylsulfinyl, or benzylsulfonyl, alkyl or alkenyl derivatives wherein the alkyl or alkenyl group contains at least 7 carbon atoms which are useful in killing and preventing proliferation of insects by upsetting their hormone balance.

3 Claims, No Drawings

PHENYL DERIVATIVES

CROSS REFERENCE TO RELATED APPLICATIONS

This is a division of application Ser. No. 279,897 filed Aug. 11, 1972 now U.S. Pat. No. 3,879,429, which is a continuation-in-part application of Ser. No. 30,295 filed Apr. 20, 1970 now U.S. Pat. No. 3,944,531.

SUMMARY OF THE INVENTION

In accordance with this invention, it has been found that compounds of the formula

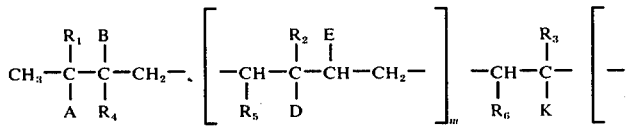

wherein $R_1$ is methyl or ethyl; $R_2$ and $R_3$ are hydrogen, methyl or ethyl; $R_4$ is hydrogen or methyl; $R_5$ and $R_6$ are hydrogen or lower alkyl; A is individually hydrogen, hydroxy or halogen; B, D and K are individually hydrogen or halogen; E and L are individually hydrogen; with A and B taken together forming a carbon to carbon bond; an oxygen bridge or sulfur bridge; with D and E taken together forming a carbon to carbon bond; and with K and L taken together forming a carbon to carbon bond; X is oxo, thio, sulfinyl, sulfonyl, —O—CH$_2$—, —S—CH$_2$ or

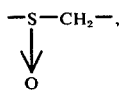

W and Y are individually hydrogen, halogen, lower alkyl or lower alkoxy; Z is hydrogen, halogen, lower alkyl, formyl, cyano, lower alkylcarbonyl, hydroxy-lower alkyl, lower alkoxymethylene, aryloxymethylene, aralykoxymethylene, carbamyl and lower alkyl substituted carbamyl; and W taken together with either Y or Z when they are substituted on adjacent carbon atoms form ethylenedioxy, propylenedioxy, vinylenedioxy or 1,3-butadien-1,4-ylene; $m$ and $n$ are 0 or 1; and the dotted lines can be optionally hydrogenated, with the proviso that when $n$ is 0, K is hydrogen; and with the further proviso that when X is oxo and K and L form a carbon to carbon bond, at least one of W, Y and Z is other than hydrogen, and Z is other than lower alkylcarbonyl;

upset the hormone balance of pests such as insects to prevent them from growing and reproducing.

The compounds of formula I are prepared through the condensation of a halide of the formula:

wherein $R_1$, $R_2$, $R_3$, $R_4$, $R_5$, $R_6$, $m$ and $n$ are as above; and A', B', D', E and L are individually hydrogen; A' taken together with B' form a carbon to carbon bond, an oxygen bridge or a sulfur bridge; and D taken together with E and K' taken together with L form a carbon to carbon bond;

with a compound of the formula:

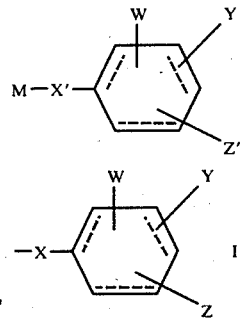

wherein M is a metal of Group 1 in the periodic table; X' is —O—, —O—CH$_2$—, —S—, or —S—CH$_2$—; and W and Y are as above; Z' is hydrogen, halogen, lower alkyl, formyl, cyano, lower alkylcarbonyl, hydroxy-lower alkyl, lower alkoxycarbonyl, aryloxycarbonyl, aralkoxycarbonyl, lower alkoxymethylene, aryloxymethylene, aralkoxymethylene, carbamyl and lower alkyl-substituted carbamyl; W taken together with either Y or Z' when they are substituted on adjacent carbon atoms form ethylenedioxy, propylenedioxy, vinylenedioxy or 1,3-butadien-1,4-ylene; and the dotted lines can be optionally hydrogenated;

oxidizing or reducing an aldehyde obtained if desired, amidating an acid obtained or an ester, esterifying an alcohol obtained if desired and, also if desired, subjecting a derivative of formula I to hydrogenation, oxidation, epoxidation, episulphidation, halogenation, hydrohalogenation or hydroxyhalogenation.

Where in the compound of formula II, K' and L form a carbon to carbon bond and in the compound of formula III X' is oxo, at least one of W, Y and Z' in the compound of formula III is other than hydrogen and Z' in the compound of formula III is other than lower alkylcarbonyl.

DETAILED DESCRIPTION OF THE INVENTION

The term, "halogen" as used throughout this application, includes all four halogens, i.e., bromine, chlorine, fluorine and iodine. As used throughout this application, the term "lower alkyl" comprehends both straight and branched chain saturated hydrocarbon groups containing from 1 to 6 carbon atoms, such as methyl, ethyl, propyl, isopropyl, etc. The term "lower alkoxy" comprehends lower alkoxy groups containing from 1 to 6 carbon atoms such as methoxy, propoxy, ethoxy, etc.

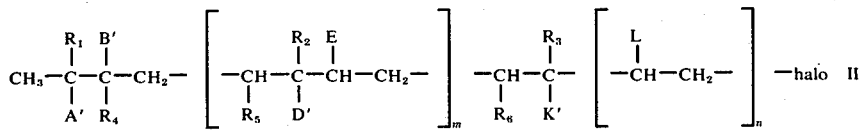

The term "aryl", as used throughout the application, includes mono-nuclear aryl groups such as phenyl which can be unsubstituted or substituted in 1 or more positions with a hydroxy, methylenedioxy, halogen, nitro, lower alkyl or a lower alkoxy substitutent, and polynuclear aryl groups such as naphthyl, anthryl, phenanthryl, azulyl, etc. which may be substituted with 1 or more of the aforementioned groups. The term "aryloxy carbonyl" comprehends aryloxy-carbonyl groups wherein the aryl moiety is defined as above. The preferred aryloxy carbonyl group is phenoxy-carbonyl. The term "aralkyloxy carbonyl" comprehends aralkoxy-carbonyl groups wherein aryl is defined as above and the alkyl is lower alkyl. The preferred aralkoxy-carbonyl group is benzyloxycarbonyl.

The term "alkoxycarbonyl" as utilized herein includes lower alkoxycarbonyl groups wherein lower alkoxy is defined as above. Among the preferred lower alkoxycarbonyl groups are included methoxycarbonyl, ethoxycarbonyl and isopropoxycarbonyl. The term "lower alkylcarbonyl" as defined herein includes the lower alkylcarbonyl groups wherein lower alkyl is defined as above. Among the preferred lower alkylcarbonyl groups are included methylcarbonyl and ethylcarbonyl. The terms "oxo" and "thio" define oxygen and sulphur with two bonds (—O— and —S—).

The aryloxymethylene group as used herein incudes aryloxymethylene groups wherein aryl is defined as above. Among the preferred aryloxymethylene groups is included phenyloxymethylene. The term "aralkoxymethylene" as used herein includes arloweralkyloxymethylene wherein aryl and lower alkyl are defined as above. The preferred aralkyloxymethylene in accordance with this invention is benzyloxymethylene. The term "alkoxymethylene" includes lower alkoxymethylene groups wherein lower alkyl is defined as above. Among the preferred lower alkoxymethylene groups are included methoxymethylene, ethoxymethylene or isopropoxymethylene. The carbamyl group can be mono-substituted or disubstituted by lower alkyl. Among the preferred lower alkyl-substituted carbamyl groups which can be utilized in accordance with this invention are included methylcarbamyl, N,N-dimethylcarbamyl, ethylcarbamyl, N,N-diethylcarbamyl and isopropylcarbamyl.

The compounds of formula I are useful in the control of pests such as *Tineola biselliella* (clothes moth), *Ephestia kuhniella* (meal moth), *Dysdercus cingulatus* (cotton bug) *Blatella germanica* (cockroach).

In contrast to most of the known pest-control agents which kill, disable or repell the pests by acting as contact poisons and feed poisons, the compounds of formula I above prevent maturation and proliferation of these pests by interferring with their hormonal system. In insects, for example, the formation into the imago, the laying of viable eggs and the development of laid normal eggs is disturbed. Furthermore, the sequence of generations is interrupted and the insects are indirectly killed.

The compounds of formula I above are practically non-toxic to vertebrates. The toxicity of these compounds is greater than 1000 mg/kg body weight. Moreover, these compounds are readily degraded and the risk of accumulation is therefore excluded. Therefore, these compounds can be used without fear of danger in the control of pests in animals, plants, foods and textiles.

Generally, in controlling invertebrate animals, the compounds of formula I above thereof are applied to the material to be protected, e.g., foodstuffs, feeds, textiles, plants in concentrations of from about $10^{-3}$ to $10^{-8}$ gm/cm$^2$ of the material to be protected. Generally, it is preferred to utilize the compounds of formula I above in a composition with a suitable inert carrier. Any conventional inert carrier can be utilized.

The compound of formula I can, for example, be used in the form of emulsions, suspensions, dusting agents, solutions or aerosols. In special cases, the materials to be protected (e.g., foodstuffs, seeds, textiles and the like) can also be directly impregnated with the appropriate compound or with a solution thereof. Moreover, the compounds can also be used in a form which only releases them by the action of external influences (e.g., contact with moisture) or in the animal body itself.

The compound of formula I above can be used as solutions suitable for spraying on the material to be protected which can be prepared by dissolving or dispersing these compounds in a solvent such as mineral oil fractions; cold tar oils; oils of vegetable or animal origins; hydrocarbons such as naphthalenes; ketones such as methyl ethyl ketone; or chlorinated hydrocarbons such as tetrachloroethylene, tetrachlorobenzene, and the like. The compounds of formula I above can also be prepared in forms suitable for dilution with water to form aqueous liquids such as, for example, emulsion concentrates, pastes or powders. The compounds of formula I above can be combined with solid carriers for making dusting or strewing powders as, for example, talc, kaolin, bentonite, calcium carbonate, calcium phosphate, etc. The compositions containing the compound of formula I above can contain, if desired, emulsifiers, dispersing agents, wetting agents, or other active substances such as fungicides, bacteriacides, nematocides, fertilizers and the like. These materials which are to be protected act as bait for the insect. In this manner, the insect, by contacting the material impregnated with the compound of formula I above, also contacts the compound of formula I above.

It will be appreciated from the foregoing that the invention also includes within its scope an agent useful for the control of pests which contains as an essential active ingredient or essential active ingredients one or more of the phenyl derivatives of formula I in association with a compatible carrier material. In addition, the invention includes within its scope a method of rendering a locus subject to or subjected to attack by pests immune to or free from such attack, said method comprising applying to said locus an agent as hereinbefore defined or one or more of the phenyl derivatives of formula I.

Among the phenyl derivatives which are included within formula I are the following:

a. derivatives of the general formula:

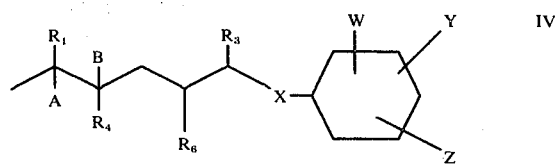

wherein $R_1$, $R_3$, $R_4$, $R_6$, A, B, X, W, Y and Z are as above; and the dotted bonds can be hydrogenated, b. derivatives of the general formula:

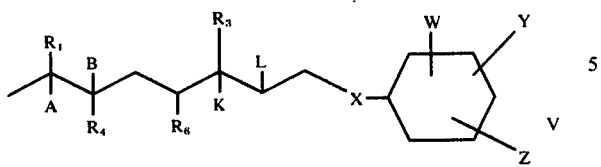

wherein $R_1$, $R_3$, $R_4$, $R_6$, A, B, K, L, X, W, Y and Z are as above; and the dotted bonds can be hydrogenated, c. derivatives of the general formula:

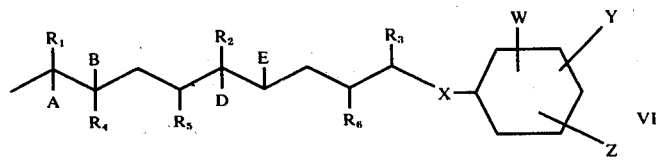

wherein $R_1$, $R_2$, $R_3$, $R_4$, $R_5$, $R_6$, A, B, D, E, X, W, Y and Z are as above; and the dotted bonds can be hydrogenated, and d. derivatives of the general formula:

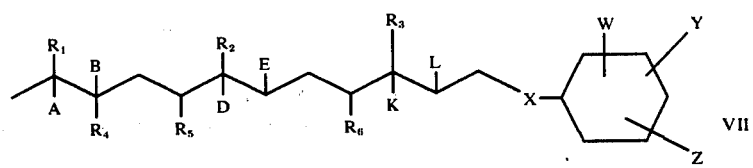

wherein $R_1$, $R_2$, $R_3$, $R_4$, $R_5$, $R_6$, A, B, D, E, K, L, X, W, Y and Z are as above and the dotted bonds can be hydrogenated.

With regard to formulae I, IV, V, VI, and VII, the preferred derivatives are those in which W signifies hydrogen, Y has the significance given earlier and Z signifies hydrogen, halogen, lower alkyl, formyl, lower alkoxymethylene, phenyloxymethylene, benzyloxymethylene or carbamyl (which may be lower alkyl-susbtituted) or Y and Z when present on adjacent carbon atoms together signify an ethylenedioxy, propylenedioxy, vinylenedioxy or 1,3-butadien-1,4-ylene group. Also preferred among the compounds of formula I, IV, V, VI, and VII are those compounds where the dotted lines are not hydrogenated.

Especially preferred classes of phenyl derivatives of the formula IV are compounds having the formula:

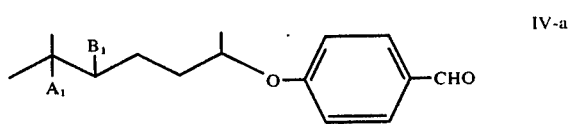

wherein $A_1$ is hydrogen or chlorine and $B_1$ is hydrogen or $A_1$ and $B_1$ taken together form a carbon to carbon bond or an oxygen bridge.

Especially preferred among the compounds of formula V are those compounds having the formulae:

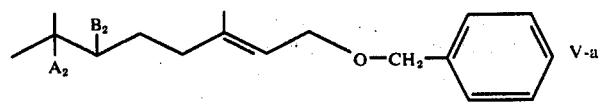

wherein $A_2$ and $B_2$ taken together form a carbon to carbon bond or an oxygen bridge;

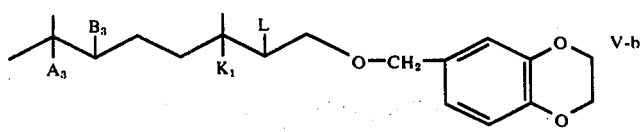

wherein $A_3$, $B_3$, $K_1$ and L are hydrogen; or $A_3$ and $B_3$ taken together form a carbon to carbon bond or oxygen bridge; and $K_1$ and L taken together form a carbon to carbon bond;

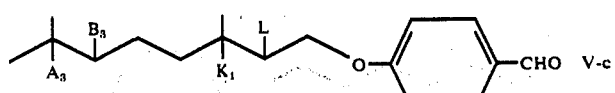

wherein $A_3$, $B_3$, $K_1$ and L are as above;

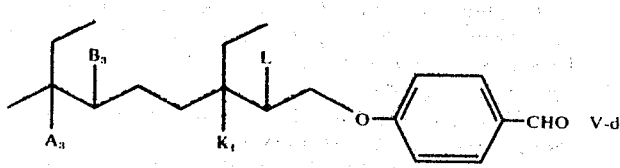 V-d wherein $A_3$, $B_3$, $K_1$ and L are as above;

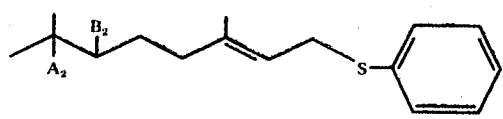 V-e wherein $A_2$ and $B_2$ are as above;

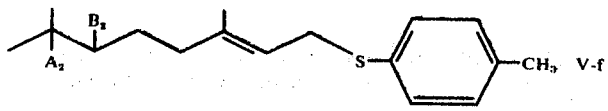 V-f wherein $A_2$ and $B_2$ are as above;
and the corresponding sulphinyl derivatives,

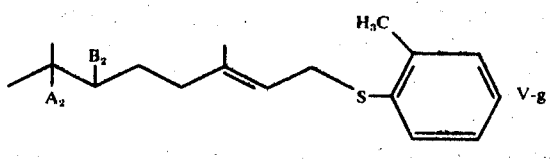 V-g wherein $A_2$ and $B_2$ are as above;
and the corresponding sulphinyl derivatives; and compounds of the formula

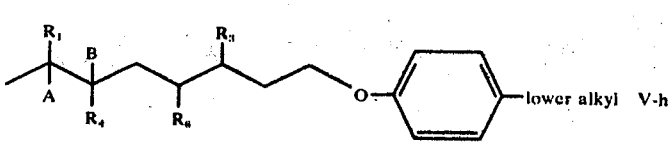 V-h wherein $R_1$, $R_3$, $R_4$, $R_6$, A and B are as described above.

Especially preferred among the compounds of formula V above is the compound having the formula:

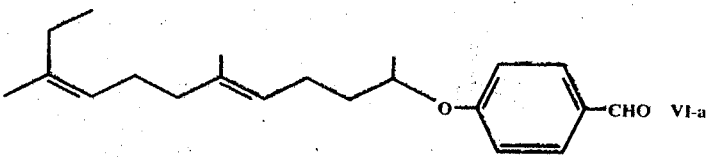 VI-a

Especially preferred among the compounds of formula VII above are the compounds having the formula:

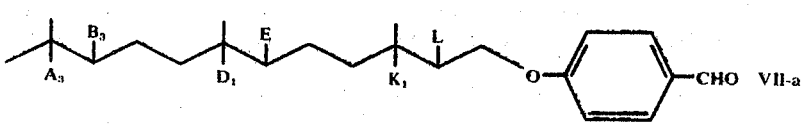 VII-a wherein $A_3$, $B_3$, $D_1$, E, $K_1$ and L are hydrogen; or $A_3$ and $B_3$ taken together are a carbon to carbon bond or an oxygen bridge; and $D_1$ taken together with E, and $K_1$ taken together with L form a carbon to carbon bond, and

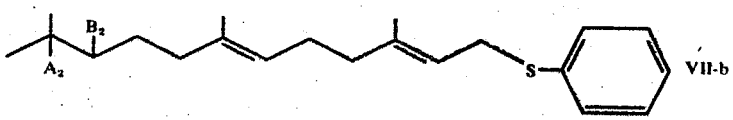 VII-b wherein $A_2$ and $B_2$ are as above.

Examples of some of the preferred phenyl derivatives of formula I are the following:

p-[(1,5-dimethyl-hexyl)-oxy]-N,N-diethyl-benzamide;
p-[(1,5-dimethyl-hexyl)-oxy]-N,N-diethyl-m-methoxybenzamide;
p-[(1,5-dimethyl-hexyl)-oxy]-benzaldehyde;
m-[(1,5-dimethyl-hexyl)-oxy]-anisole;

p-[(1,5-dimethyl-hexyl)-oxy]-benzyl alcohol;
p-[(1,5-dimethyl-hexyl)-oxy]-anisole;
p-[(1,5-dimethyl-hexyl)-oxy]-N,N-diisobutyl-benzamide;
p-[(1,5-dimethyl-hexyl)-oxy]-acetophenone;
p-[(1,5-dimethyl-hexyl)-oxy]-α-propoxy-toluene;
p-[(1,5-dimethyl-hexyl)-oxy]-benzonitrile;
o-bromo-phenyl 1,5-dimethyl-hexyl ether;
1-[(1,5-dimethyl-hexyl)-oxy]-3,5-dimethoxy-benzene;
2,4-dichlorophenyl 3,7-dimethyl-octyl ether;
4-[(1,5-dimethyl-hexyl)-oxy]-3,5-dimethoxy-pentanophenone;
p-[(3,7-dimethyl-2,6-octadienyl)-oxy]-N,N-diethyl-m-methoxybenzamide;
p-[(6,7-epoxy-3,7-dimethyl-oct-2-enyl)-oxy]-N,N-diethyl-m-methoxybenzamide;
p-[(1,4,5-trimethyl-hex-4-enyl)-oxy]-N,N-diethyl-m-methoxybenzamide;
p-[(4,5-epoxy-1,4,5-trimethyl-hexyl)-oxy]-N,N-diethyl-m-methoxybenzamide;
benzyl 3,7-dimethyl-octa-2,6-dienyl ether;
6-[[(6,7-epoxy-3,7-dimethyl-oct-2-enyl)-oxy]-methyl]-1,4-benzodioxan;
3,7-dimethyl-octa-2,6-dienyl phenyl sulfide;
6,7-epoxy-3,7-dimethyl-oct-2-enyl phenyl sulfide;
3,7-dimethyl-octa-2,6-dienyl phenyl sulfoxide; benzyl 3,7-dimethyl-octa-2,6-dienyl sulfide;
benzyl 6,7-epoxy-3,7-dimethyl-oct-2-enyl sulfoxide;
3,7,11-trimethyl-dodeca-2,6,10-trienyl phenyl sulfide;
10,11-epoxy-3,7,11-trimethyl-dodeca-2,6-dienyl phenyl sulfide;
3,7,11-trimethyl-dodeca-2,6,10-trienyl 2-naphthyl sulfoxide;
10,11-epoxy-3,7,11-trimethyl-dodeca-2,6-dienyl phenyl sulfoxide;
10,11-epoxy-3,7,11-trimethyl-dodeca-2,6-dienyl phenyl sulfone; and
10,11-epoxy-3,7,11-trimethyl-dodeca-2,6-dienyl-2-naphthyl sulfone.

The halide starting materials of formula II can be subdivided into four classes as follows:
a. halides of the general formula:

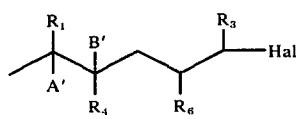

wherein $R_1$, $R_3$, $R_4$, $R_6$, $A'$, $B'$ and Hal are as above;
b. halides of the general formula:

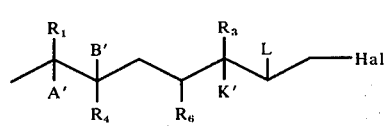

wherein $R_1$, $R_3$, $R_4$, $R_6$, $A'$, $B'$, $K'$, L and Hal are as above;
c. halides of the general formula:

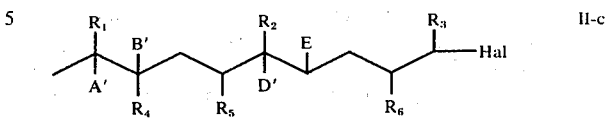

wherein $R_1$, $R_2$, $R_3$, $R_4$, $R_5$, $R_6$, $A'$, $B'$, $D'$, and E are as above; and Hal is a halogen;
and
d. halides of the general formula:

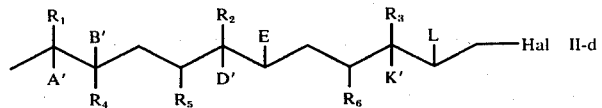

wherein $R_1$, $R_2$, $R_3$, $R_4$, $R_5$, $R_6$, $A'$, $B'$, $D'$, E, $K'$, L and Hal are as above.

In accordance with a preferred embodiment of this invention, a halide of formula II-a, II-b, II-c or II-d is reacted with a compound of formula III in which W signifies hydrogen, Y has the significance given earlier and Z' signifies hydrogen, halogen, lower alkyl, formyl, lower alkoxycarbonyl, phenyloxycarbonyl, benzyloxycarbonyl, lower alkoxymethylene, phenyloxymethylene, benzyloxymethylene or carbamyl (which may be lower alkyl-substituted) or Y and Z' when present on adjacent carbon atoms taken together form an ethylenedioxy, propylenedioxy, vinylenedioxy or 1,3-butadien-1,4-ylene group.

Especially preferred embodiments of the process provided by the invention comprise:
e. reacting a halide of the general formula:

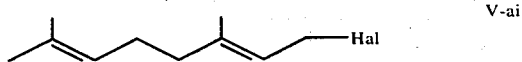

wherein Hal is as above; and the dotted bond can be hydrogenated,
with an alkali metal salt of p-hydroxybenzaldehyde and, if desired hydrogenating, epoxidizing or hydrochlorinating the product obtained;
f. reacting a halide of the general formula:

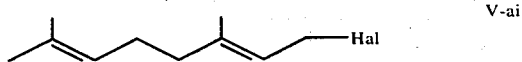

wherein Hal is as above;
with an alkali metal salt of benzyl alcohol and, if desired, the product obtained is epoxidized at the terminal unsaturation;
g. reacting a halide of the general formula:

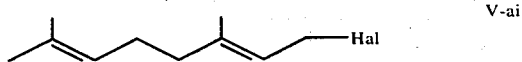

wherein Hal is as above; and the dotted bonds can be hydrogenated;

with an alkali metal salt of 6-hydroxymethyl-1,4-benzodioxan and, if desired, subjecting the product obtained to hydrogenation or epoxidation at the terminal unsaturation;

h. reacting a halide of general formula V-bi hereinbefore with an alkali metal salt of -hydroxybenzaldehyde and, if desired, subjecting the product obtained to hydrogenation or epoxidation at the terminal unsaturation;

i. reacting a halide of the general formula:

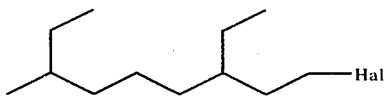

V-di wherein Hal is as above; and the dotted bonds can be hydrogenated;
with an alkali metal salt of p-hydroxybenzaldehyde and, if desired, subjecting the product obtained to hydrogenation or epoxidation at the terminal unsaturation;

j. reacting a halide of formula V-ai above, with an alkali metal salt of thiophenol and, if desired, submitting the product obtained to oxidation or epoxidation at the terminal unsaturation;

k. reacting a halide of formula V-ai hereinbefore with an alkali metal salt of thio-p-cresol and, if desired, submitting the product obtained to oxidation and/or epoxidation at the terminal unsaturation;

l. reacting a halide of formula V-ai hereinbefore with an alkali metal salt of thio-o-cresol and, if desired, submitting the product obtained to oxidation and/or epoxidation at the terminal unsaturation;

m. reacting a halide of the general formula:

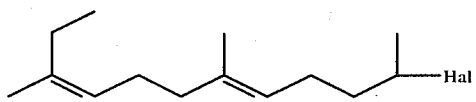

VI-ai wherein Hal is as above;
with an alkali metal salt of p-hydroxybenzaldehyde;
n. reacting a halide of the general formula:

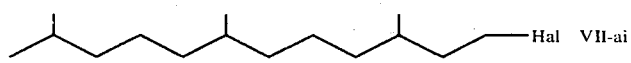

VII-ai wherein Hal is as above; and the dotted bonds can be hydrogenated;
with an alkali metal salt of p-hydroxybenzaldehyde and, if desired, subjecting the product obtained to hydrogenation or epoxidation at the terminal unsaturation; and o. reacting a halide of the general formula:

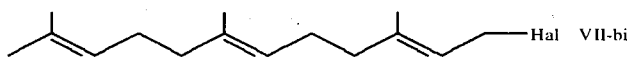

VII-bi wherein Hal is as above;
with an alkali metal salt of thiophenol and, if desired, subjecting the product obtained to oxidation and/or epoxidation at the terminal unsaturation.

The halide starting materials of formula II and the starting materials of formula III are known substances and they can be reacted with each other to produce a compound of the formula I above in accordance with methods known per se.

For example, a halide of formula II preferably a chloride or bromide, is expediently dissolved in an inert organic solvent and the solution allowed to act on a compound of formula III (formed in statu nascendi). The compound of formula III (an alkali metal salt) can advantageously be formed by reacting the corresponding phenol, alcohol, thiophenol or thioalcohol with an alkali metal hydride alkali metal alcoholate or alkali metal hydroxide, preferably sodium hydride, a sodium alcoholate or sodium hydroxide in a known manner. The salt formation and the reaction of the salt with the halide are expediently carried out in the presence of a suitable inert organic solvent. When sodium hydride is used, suitable solvents are, for example, dioxan, tetrahydrofuran, dimethylformamide or diethyl ether, when sodium methylate is used a suitable solvent is for example, methanol or when sodium hydroxide is used suitable solvents are for example, methanol, ethanol or acetone. The reaction of the halide with a phenol, alcohol, thiophenol or thioalcohol can also be carried out in the presence of a carbonate, preferably potassium carbonate.

The reaction of a halide of formula II with a compound of formula III is expediently carried out at a temperature between 0° C. and the boiling temperature of the reaction mixture, advantageously in the presence of hexamethyl phosphoric acid triamide. The reaction mixture can be worked up in a conventional manner. For example, it can be poured onto ice and extracted with diethyl ether, the ether extract washed with water, dried and evaporated. The resulting derivative of formula I can be purified by adsorption; for example, on Kieselgel or aluminum oxide.

When Z, in the compound of formula I above is formyl, this compound can be oxidized to the corresponding acid or reduced to the corresponding alcohol in a known manner.

The oxidation of the formyl group can advantageously be carried out at room temperature with the aid of silver oxide formed in an aqueous medium from silver nitrate and sodium hydroxide. After the oxidation, the aqueous solution is extracted with diethyl ether and the ether extract is discarded. By acidification of the aqueous phase, the sodium salt present therein is converted into the free acid which can be extracted (e.g., with diethyl ether or methylene chloride) and isolated from the extract in a conventional manner. The acid obtained in this manner can be converted into an amide (which may be lower alkyl-substituted) by conventional amidation reactions.

The reduction of the formyl groups can advantageously be carried out with the aid of a metal hydride or alkyl metal hydride in an inert organic solvent. Mixed metal hydrides such as, for example, sodium borohydride or lithium aluminum hydride and, especially alkylated metal hydrides such as, for example, the dialkyl aluminium hydrides, particularly diisobutyl aluminum hydride or bis-[methoxyethyleneoxy]-sodium-aluminum hydride, are the preferred metal hydrides. Suitable solvents are, inter alia, alkanols (especially methanol) when sodium borohydride is used, diethyl ether, tetrahydrofuran or dioxan when lithium aluminum hydride is used and diethyl ether, hexane, benzene or toluene when diisobutyl aluminum hydride is used. The reduction is expediently carried out at a temperature between −20° C. and +50° C.

When Z, in the compound of formula I above is an acid group, the acid can be converted into an acid chloride by conventional means such as by treatment with thionyl chloride, preferably in the presence of pyridine. The acid halide can be transformed into an ester by reaction with an alkanol or into an acid amide by reaction with ammonia or a monosubstituted amine or a disubstituted amine utilizing conventional procedures well known in the art.

When Z, in the compound of formula I above is a hydroxy methylene group, this group can be etherified by conventional procedures such as by reaction with an alkyl halide (e.g., with ethyl iodide) in the presence of a base, preferably in the presence of sodium hydride, in a solvent such as dioxan, tetrahydrofuran, 1,2-dimethoxyethane, dimethylformamide or also in the presence of an alkali metal alcoholate in an alkanol at a temperature of from 0° C. to room temperature.

When Z' in a compound of formula III is a lower alkoxycarbonyl, aryloxycarbonyl, or aralkoxycarbonyl, the ester obtained is converted into an amide (which may be lower alkyl substituted). This conversion can be carried out, for example, by treating the ester with an appropriate dialkylaminelithium compound. The dialkylaminelithium needed for this treatment can expediently be prepared by dissolving a dialkylamine (e.g., diethylamine) in diethyl ether and mixing the resulting solution in the cold (preferably at −10° C to −20° C) with a solution of butyl-lithium in hexane or tetrahydrofuran and subsequently allowing the mixture to react. The diethylamine-lithium obtained is advantageously reacted with the ester at room temperature.

If desired, the derivatives of formula I in which A and B taken together, D and E taken together and K and L taken together form a carbon to carbon bond can be hydrogenated, oxidized, halogenated, epoxidized, episulfidized, hydrohalogenated, or hydroxyhalogenated in accordance with methods known per se. In addition, derivatives of formula I in which Z signifies formyl can be oxidized or reduced, if desired, in accordance with methods known per se.

The hydrogenation of unsaturated derivatives of formula I can be carried out at normal or elevated pressure with catalytically activated hydrogen, expediently at a temperature between room temperature and the boiling temperature of the solvent used. Suitable catalysts are, for example, Raney-nickel or, especially, noble metals such as, for example, palladium or platinum. Suitable solvents include ethyl acetate, alkanols such as methanol and ethanol and glacial acetic acid. If the hydrogenation is carried out in ethyl acetate or in an alkanol (e.g., methanol) under the conditions described hereinabove, the side chain is almost exclusively saturated. If, on the other hand, the hydrogenation is carried out in the presence of glacial acetic acid, not only the side chain but also the phenyl ring is saturated. The corresponding cyclohexyl derivatives are thus obtained and they can be separated by distillation from cleavage products of the hydrogen atom which may also be formed. It should be noted that only sulphur free-compounds can advantegeously be subjected to this type of hydrogenation.

Thioethers obtained can be oxidized to the corresponding sulfinyl or sulfonyl derivatives by oxidation. Particularly suitable oxidizing agents are organic peracids, preferably m-chloroperbenzoic acid. The oxidation is advantageously carried out in an inert organic solvent, especially in methylene chloride at a temperature between 0° C. and room temperature. If 1 mole of peracid is used for each mole of thioether, the corresponding sulfinyl derivative is obtained. If 2 moles of peracid are used for each mole of thioether, the corresponding sulfonyl derivative is obtained.

The epoxidation of derivatives of formula I can expediently be carried out by dissolving the derivative concerned in an inert solvent (especially in a halogenated hydrocarbon such as methylene chloride or chloroform) and treating the solution obtained with an organic peracid (e.g., with perbenzoic acid, m-chloroperbenzoic acid or perphthalic acid) at a temperature between 0° C. and room temperature. Alternatively, the derivative concerned can be suspended in water and treated with an appropriate amount of an inert solvent (e.g., with dioxan, tetrahydrofuran or 1,2-dimethoxyethane) such that a homogenous concentrated solution is obtained. N-Bromosuccinimide is then introduced portionwise into this solution at a temperature between 0° C. and room temperature. The resulting bromohydrin can be smoothly converted into the desired epoxide by the action of alkali, especially by the action of sodium methylate in methanol.

The introduction of a sulfur bridge into derivatives of formula I can be effected in various ways. If, for example, thiourea is allowed to act on a halohydrin (preferably on the bromohydrin) of a derivative of formula I there is firstly formed an isothiouronium salt. This salt is also formed when thiourea is allowed to act on an epoxide of formula I, a temperature of from 0° to 30° C. in the presence of a mineral acid. The isothiouronium salts obtained can be readily converted into the desired epithio derivatives of formula I by treatment with a base.

The hydrohalogenation of a derivative of formula I is expediently carried out by dissolving the derivative concerned in an inert organic solvent (e.g., an ether, especially ethyl ether, or an alkanol, especially methanol or ethanol), saturating the solution obtained with a hydrogen halide either at a low temperature (e.g., a temperature between −20° C. and −25° C.) or at a temperature between 0° C. and room temperature and working up the reaction solution in a conventional manner; for example, by carefully evaporating the solution under reduced pressure, dissolving the concentrate in diethyl ether, deacidifying, drying and evaporating the extract. If the hydrohalogenation is carried out within the aforementioned low temperature range, the derivative used is almost exclusively monohydrohalogenated at the terminal unsaturation. On the other hand, if the hydrohalogenation is carried out at temperatures around and above 0° C. the elements of hydrogen halide are added to all double bonds present. Derivatives having an allylic ether group are less suitable for the hydrohalogenation described hereinbefore, since the ether is, in part, cleaved under the hydrohalogenation conditions specified earlier.

As described hereinbefore in the case of the epoxidation, the hydroxyhalogenation of a derivative of formula I can be carried out by treating the derivative concerned with an N-halosuccinimide (especially with N-bromosuccinimide) and isolating the halohydrin formed.

The halogenation of a terminal double bond in the compound of formula I can be carried out by conventional halogenation procedures. In accordance with a preferred embodiment of this invention, the compound of formula I is dissolved in a lower aliphatic carboxylic acid (preferably glacial acetic acid) or in a chlorinated lower hydrocarbon (preferably carbon tetrachloride) and then treated with a solution of the appropriate halogen in the same solvent. The resulting mixture can be allowed to stand in the presence of an alkali acetate (especially sodium acetate) at a temperature between about 0° C. and 60° C., advantageously at room temperature. The mixture can be worked up by conventional procedures. For example, the mixture can be diluted with water, extracted with diethyl ether, the ether extract washed with water and sodium bicarbonate solution, dried and evaporated. The derivative which remains behind can be purified by crystallization or by chromatography on Kieselgel (silica gel).

Insofar as the side chain is unsaturated, the derivatives of formula I are obtained according to the process as a cis/trans isomer mixture. The mixture can, for example, be separated into the individual isomeric forms by adsorption on a material having selective activity. For example, the isomer mixture can be dissolved in an inert organic solvent (e.g., in hexane, ether or acetic acid ethyl ether) and adsorbed on Kieselgel. The isomers adsorbed in different zones can be eluted with one of the solvents named hereinbefore or a mixture thereof and isolated. In individual cases, the isomer mixture can also be separated by fractional distillation or by fractional crystallization.

The following examples are illustrative but not limitative of this invention. In the examples, the suspension of the hydride mineral oil is percent by weight. The ether utilized in these exampls was diethyl ether. The petroleum ether utilized in these examples has a boiling point of from 40° C. to 45° C.

EXAMPLE 1

In an inert gas atmosphere, 15.8 g of a 50% suspension of sodium hydride in mineral oil are washed with two 50ml portions of tetrahydro-furan, then introduced into 100 ml of tetrahydro-furan and treated dropwise with a solution of 40 g of p-hydroxy-benzaldehyde in 150 ml of tetrahydro-furan. 78.0 g of 2-bromo-6-methyl-heptane in 150 ml of hexamethylphosphoric triamide are subsequently added dropwise, then the resulting mixture is heated under reflux conditions for 2 hours, cooled, poured onto ice and exhaustively extracted with diethyl ether. The ether extract is washed with water, dried over sodium sulphate and evaporated under reduced pressure. The residual oily p-[(1,5-dimethyl-hexyl)-oxy]-benzaldehyde is purified by adsorption on Kieselgel; boiling point = 155°–158° C/0.1 mmHg.

EXAMPLE 2

In the same manner as Example 1:

2-bromo-6-methyl-heptane was reacted with o-bromo-phenol to obtain o-bromo-phenyl 1,5-dimethyl-hexyl ether (boiling point =190°–193° C/17 mmHg);

2-bromo-6-methyl-heptane was reacted with 3,5-dimethoxy-phenol to obtain 1-[(1,5-dimethyl-hexyl)-oxy]-3,5-dimethoxy-benzene (boiling point = 135° C/0.4 mmHg);

2-bromo-6-methyl-heptane was reacted with 3-methoxy-4-hydroxy-5-bromo-benzaldehyde to obtain 5-bromo-4-[(1,5-dimethyl-hexyl)-oxy]-m-anisaldehyde (boiling point = 190°–193° C/0.1 mmHg);

2-bromo-6-methyl-heptane was reacted with p-hydroxy-benzonitrile to obtain p-[(1,5-dimethyl-hexyl)-oxy]-benzonitrile (boiling point = 165°–168° C/1.0 mmHg);

2-bromo-6-methyl-heptane was reacted with m-methoxy-phenol to obtain m-[(1,5-dimethyl-hexyl)-oxy]-anisole (boiling point =210°–212° C/12 mmHg);

2-bromo-6-methyl-heptane was reacted with p-hydroxy-acetophenone to obtain p-[(1,5-dimethyl-hexyl)-oxy]-acetophenone (boiling point = 200° C/1.0 mmHg);

geranyl bromide was reacted with vanillic acid N,N-diethyl amide to obtain p-geranyloxy-m-methoxy-N,N-diethyl-benzamide (boiling point = 180°/0.05 mmHg);

2-bromo-1,4,5-trimethyl-hex-4-ene was reacted with vanillic acid N,N-diethyl amide to obtain p-[(1,4,5-trimethyl-hex-4-enyl)-oxy]-m-methoxy-N,N-diethyl-benzamide (boiling point = 160°–162° C/0.02 mmHg, $n_D^{28}$ = 1.5185);

2-bromo-6-methyl-heptane was reacted with vanillic acid N,N-diethyl amide to obtain p-[(1,5-dimethyl-hexyl)-oxy]-m-methoxy-N,N-diethyl-benzamide (boiling point = 180°–182° C/0.1 mmHg);

2-bromo-6-methyl-heptane was reacted with p-methoxy-phenol to obtain p-[(1,5-dimethyl-hexyl)-oxy]-anisole (boiling point =170°–172° C/1.0 mmHg);

and 2-bromo-6-methyl-heptane was reacted with p-hydroxy- benzonitrile to obtain p-[(1,5-dimethyl-hexyl)-oxy]-benzonitrile (boiling point = 165°–168° C/1.0 mmHg).

EXAMPLE 3

5.5 g of p-[(1,4,5-trimethyl-hex-4-enyl)-oxy]-m-methoxy-N,N-diethyl-benzamide are dissolved in 50 ml of ethanol and hydrogenated under normal conditions in the presence of 0.1 g of platinum oxide. After the uptake of 1 mol of hydrogen, the hydrogenation is terminated and the catalyst is filtered off. The clear filtrate is evaporated under reduced pressure. The residual oily p-[(1,4,5-trimethyl-hexyl)-oxy]-m-methoxy-N,N-diethyl-benzamide is purified by adsorption on Kieselgel; boiling point =158°–160° C/0.02 mmHg; $n_D^{26}$ = 1.5060.

EXAMPLE 4

A solution of 2 g of p-geranyloxy-m-methoxy-N,N-diethyl-benzamide in 150 ml of methylene chloride is treated dropwise at 0° C with a solution of 1.2 g of 30% by weight m-chloro-per-benzoic acid in 100 ml of methylene chloride. After 15 minutes, the resulting mixture is successively washed with a 2% by weight sodium bisulphite aqueous solution, a 5% by weight sodium bicarbonate aqueous solution and water, dried over sodium sulphate and evaporated under reduced pressure. The residual p-[(6,7-epoxy-3,7-dimethyl-oct-2-enyl)-oxy]-m-methoxy-N,N-diethyl-benzamide is purified by adsorption on Kieselgel; $n_D^{24} = 1.5294$.

In a manner analogous to the foregoing, from p-[(1,4,5-trimethyl-hex-4-enyl)-oxy]-m-methoxy-N,N-diethyl-benzamide there is obtained p-[(4,5-epoxy-1,4,5-trimethyl-hexyl)-oxy]-m-methoxy-N,N-diethyl-benzamide ($n_D^{25} = 1.5108$).

EXAMPLE 5

3.4 g of sodium are dissolved in 150 ml of absolute ethanol. While stirring at room temperature, the solution is treated with 18.6 g of thio-p-cresol. The resulting mixture is further stirred at room temperature for 30 minutes, then treated with 29 g of 2-bromo-6-methyl-heptane under reflux conditions for 30 minutes, cooled and treated with 300 ml of water and 300 ml of diethyl ether. The ether phase is separated off, washed with water, and dried over sodium sulphate and evaporated under reduced pressure. The residual 1,5-dimethyl-hexyl p-tolyl sulphide boils at 102°–105° C/0.5 mmHg.

EXAMPLE 6

23.7 g of 1,5-dimethyl-hexyl p-tolyl sulphide are dissolved in 250 ml of methylene chloride and treated portionwise at 0°–5° C with 13 g of m-chloro-perbenzoic acid. The resulting mixture is further stirred at room temperature for 1 hour and subsequently diluted with 200 ml of methylene chloride. The solution obtained is successively washes with 0.1-N sodium hydroxide solution and water. The methylene chloride phase is separated off, dried over sodium sulphate and evaporated under reduced pressure. The residual 1,5-dimethyl-hexyl p-tolyl sulphoxide is purified by absorption on Kieselgel; $n_D^{25} = 1.5248$.

Example 7

23.7 g of 1,5-dimethyl-hexyl p-tolyl sulphide are dissolved in 250 ml of methylene chloride. With stirring, the solution is treated portionwise at 0°–5° C with 36 g of m-chloro-perbenzoic acid. The resulting mixture is further stirred at room temperature for 1 hour, then diluted with 200 ml of methylene chloride. The solution obtained is successively washed with 0.1-N sodium hydroxide solution and water. The methylene chloride phase is separated off, dried over sodium sulphate and evaporated under reduced pressure. The residual 1,5-dimethyl-hexyl p-tolyl sulphone is purified by adsorption on Kieselgel; $n_D^{25} = 1.5101$.

EXAMPLE 8

50 g of a 50% suspension of sodium hydride in mineral oil are washed 3 times with hexane, then inroduced into 300 ml of N,N-dimethyl-formamide and treated with 83 g of 6-hydroxy-methyl-1,4-benzodioxan. 108 g of 1-bromo-3,7-dimethyl-octa-2,-6-diene are subsequently added dropwise and the resulting mixture is stirred at room temperature for 1 hour, then treated with 1000 ml of water and exhaustively extracted with diethyl ether. The ether extract is washed with water, dried over sodium sulphate and evaporated under reduced pressure. The residual 6-[[(3,7-dimethyl-octa-2,6-dienyl)-oxy]-methyl]-1,4-benzodioxan is purified by adsorption on Kieselgel; $n_D^{25} = 1.5285$.

EXAMPLE 9

In a manner analogous to Example 8,
2,4-dichloro-phenol is reacted with 1-bromo-3,7-dimethyl-octa-2,6-diene to produce 2,4-dichloro-phenyl 3,7-dimethyl-octa-2,-6-dienyl ether ($n_D^{25} = 1.5368$) and benzyl alcohol is reacted with 1-bromo-3,7-dimethyl-octa-2,6-diene to produce 3,7-dimethyl-octa-2,6-dienyl ether ($n_D^{25} = 1.5095$).

EXAMPLE 10

15 g of 2,4-dichloro-phenyl 3,7-dimethyl-octa-2,6-dienyl ether are dissolved in 100 ml of ethyl acetate and hydrogenated under normal conditions in the presence of 0.5 g of platinum oxide. After the uptake of 2 mol of hydrogen, the hydrogenation is terminated and the catalyst is filtered off. The clear filtrate is evaporated under pressure. The residual 2,4-dichloro-phenyl 3,7-dimethyl-octyl ether boils at 123°–125° C/0.01 mmHg.

EXAMPLE 11

In a manner described in Example 10, 6-[[(3,7-dimethyl-octa-2,6-dienyl)-oxy]-methyl]-1,4-benzodioxan is hydrogenated to produce 6-[[(3,7-dimethyl-octyl)-oxy]-methyl]-1,4-benzodioxan ($n_D^{25} = 1.5009$).

EXAMPLE 12

29.9 g of 2,4-dichloro-phenyl 3,7-dimethyl-octa-2,6-dienyl ether are dissolved in 300 ml of methylene chloride. With stirring, the solution is treated portionwise at 0° C with 21.8 g of m-chloro-perbenzoic acid. The resulting mixture is further stirred for 30 minutes at 0° C and subsequently for 30 minutes at room temperature. Methylene chloride is then added until a clear solution is obtained. This solution is successively washed with 0.5-N aqueous sodium hydroxide solution and water, dried over sodium sulphate and evaporated under reduced pressure. The residual oily 2,4-dichloro-phenyl 6,7-epoxy-3,7-dimethyl-oct-2-enyl ether is purified by adsorption on Kieselgel; $n_D^{25} = 1.5312$.

EXAMPLE 13

In a manner of Example 12,
3,7-dimethyl-octa-2,6-dienyl benzyl ether is epoxidized to produce 6,7-epoxy-3,7-dimethyl-oct-2-enyl benzyl ether ($n_D^{25} = 1.5431$); and 6-[[3,7-dimethyl-octa-2,6-dienyl)-oxy]-methyl]-1,4-benzodioxan is epoxidized to produce 6-[[(6,7-epoxy-3,7-dimethyl-oct-2-enyl))-oxy]-methyl]-1,4-benzodioxan ($n_D^{25} = 1.5529$).

EXAMPLE 14

11.5 g of sodium are dissolved in 400 ml of absolute ethanol. With stirring at room temperature, the solution is successively treated with 55 g of thiophenol and 108 g of 1-bromo-3,7-dimethyl-octa-2,6-diene. The resulting mixture is stirred at room temperature for 1 hour. Precipitated sodium bromide is then filtered off and the filtrate is evaporated, treated with 500 ml of water and extracted with ether. The ether extract is successively washed with water and aqueous sodium bicarbonate solution, dried over sodium sulphate and evaporated under reduced pressure. The residual 3,7-dimethyl-octa-2,6-dienyl phenyl sulphide boils at 140° C/0.85 mmHg.

EXAMPLE 15

In the same manner as Example 14 the following reactions are carried out:
2-thionaphthol is reacted with 1-bromo-3,7-dimethyl-octa-2,6-diene to produce 3,7-dimethyl-octa-2,6-dienyl 2-naphthyl sulphide (boiling point = 138° C/0.25 mmHg;

thio-p-cresol is reacted with 1-bromo-3,7-dimethyl-octa-2,6-diene to produce 3,7-dimethyl-octa-2,6-dienyl p-tolyl sulphide (boiling point = 116°–118° C/0.1 mmHg);

thio-m-cresol is reacted with 1-bromo-3,7-dimethyl-octa-2,6-diene to produce 3,7-dimethyl-octa-2,6-dienyl m-tolyl sulphide (b.p.122° C/0.07 mmHg);

thio-o-cresol is reacted with 1-bromo-3,7-dimethyl-octa-2,6-diene to produce 3,7-dimethyl-octa-2,6-dienyl o-tolyl sulphide (boiling point = 125° C/0.08 mmHg);

and benzyl mercaptan is reacted with 1-bromo-3,4-dimethyl-octa-2,6-diene to produce 3,7-dimethyl-octa-2,6-dienyl benzyl sulphide (boiling point = 128° C/0.08 mmHg).

EXAMPLE 16

49.2 g of 3,7-dimethyl-octa-2,6-dienyl phenyl sulphide are dissolved in 200 ml of methylene chloride and, while stirring at 0°–5° C, treated with 43.4 g of m-chloro-perbenzoic acid. The resulting mixture is further stirred at room temperature for 30 minutes. 100 ml of methylene chloride are added and the resulting solution is washed with water and with sodium bicarbonate solution, dried over sodium sulphate and evaporated under reduced pressure. The residual 3,7-dimethyl-octa-2,6-dienyl phenyl sulphoxide is purified by adsorption on Kieselgel; $n_D^{25} = 1.5491$.

EXAMPLE 17

In a manner analogous to Example 16, from 3,7-dimethyl-octa-2,6-dienyl 2-naphthyl sulphide there is obtained 3,7-dimethyl-octa-2,6-dienyl 2-naphthyl sulphoxide (melting point = 74°–76° C);

from 3,7-dimethyl-octa-2,6-dienyl p-tolyl sulphide there is obtained 3,7-dimethyl-octa-2,6-dienyl p-tolyl sulphoxide ($n_D^{25} = 1.5488$);

from 3,7-dimethyl-octa-2,6-dienyl m-tolyl sulphide there is obtained 3,7-dimethyl-octa-2,6-dienyl m-tolyl sulphoxide ($n_D^{25} = 1.5480$);

from 3,7-dimethyl-octa-2,6-dienyl o-tolyl sulphide there is obtained 3,7-dimethyl-octa-2,6-dienyl o-tolyl sulphoxide ($n_D^{25} = 1.5507$);

and from 3,7-dimethyl-octa-2,6-dienyl benzyl sulphide there is obtained 3,7-dimethyl-octa-2,6-dienyl benzyl sulphoxide ($n_D^{25} = 1.5406$).

EXAMPLE 18

26 g of 3,7-dimethyl-octa-2,6-dienyl p-tolyl sulphide are suspended 25 ml of water. The suspension is treated with tetrahydro-furan until a clear solution is formed. This solution is treated portionwise with stirring at 0°–5° C with 17.1 g of N-bromo-succinimide. The resulting mixture is stirred for 1 hour, then extracted with 600 ml of ether. The ether extract is washed with water, dried over sodium sulphate and evaporated under reduced pressure. The residual crude bromo-hydrin is treated at room temperature with a sodium ethoxide solution prepared from 2–3 g of sodium and 200 ml of ethanol and stirred for 5 hours, then exhaustively extracted with diethyl ether. The ether extract is washed with water, dried over sodium sulphate and evaporated under reduced pressure. The residual 6,7-epoxy-3,7-dimethyl-oct-2-enyl p-tolyl sulphide is purified by adsorption on Kieselgel: $n_D^{25} = 1.5410$.

EXAMPLE 19

In a manner described in Example 18:

from 3,7-dimethyl-octa-2,6-dienyl phenyl sulphide there is obtained 6,7-epoxy-3,7-dimethyl-oct-2-enyl phenyl sulphide ($n_D^{25} = 1.5560°$);

from 3,7-dimethyl-octa-2,6-dienyl 2-naphthyl sulphide there is obtained 6,7-epoxy-3,7-dimethyl-oct-2-enyl 2-naphthyl sulphide ($n_D^{25} = 1.6010$);

from 3,7-dimethyl-octa-2,6-dienyl m-tolyl sulphide there is obtained 6,7-epoxy-3,7-dimethyl-oct-2-enyl m-tolyl sulphide ($n_D^{25} = 1.5425$);

from 3,7-dimethyl-octa-2,6-dienyl o-tolyl sulphide there is obtained 6,7-epoxy-3,7-dimethyl-oct-2-enyl o-tolyl sulphide ($n_D^{25} = 1.5450$);

from 3,7-dimethyl-octa-2,6-dienyl phenyl sulphoxide there is obtained 6,7-epoxy-3,7-dimethyl-oct-2-enyl phenyl sulphoxide ($n_D^{25} = 1.5486$);

from 3,7-dimethyl-octa-2,6-dienyl 2-naphthyl sulphoxide there is obtained 6,7-epoxy-3,7-dimethyl-oct-2-enyl 2-naphthyl sulphoxide ($n_D^{25} = 1.5898$);

from 3,7-dimethyl-octa-2,6-dienyl p-tolyl sulphoxide there is obtained 6,7-epoxy-3,7-dimethyl-oct-2-enyl p-tolyl sulphoxide ($n_D^{25} = 1.5409$);

from 3,7-dimethyl-octa-2,6-dienyl m-tolyl sulphoxide there is obtained 6,7-epoxy-3,7-dimethyl-oct-2-enyl m-tolyl sulphoxide $n_D^{25} = 1.5450$);

and from 3,7-dimethyl-octa-2,6-dienyl o-tolyl sulphoxide there is obtained 6,7-epoxy-3,7-dimethyl-oct-2-enyl o-tolyl sulphoxide ($n_D^{25} = 1.5437$).

EXAMPLE 20

30 g of a 50% by weight suspension of sodium hydride in mineral oil are washed 3 times with petroleum ether, then introduced into 100 ml of N,N-dimethyl-formamide and treated at room temperature, with stirring, with 18 g of 7-hydroxymethyl-1,5-benzodioxepine. The mixture is further stirred at room temperature for 30 minutes, then treated with 28.5 g of 1-bromo-3,7,11-trimethyl-dodeca-2,6,10-triene and subsequently stirred at room temperature for 2 hours, then cooled with ice, treated with 500ml of water and extracted with ether. The ether extract is washed with water, dried over sodium sulphate and evaporated under reduced pressure. The residual 7-[[(3,7,11-trimethyl-dodeca-2-6-10-trienyl)-oxy]-methyl]-1,5-benzodioxepine is purified by adsorption on Kieselgel; $n_D^{25} = 1.5253$.

EXAMPLE 21

4 g of 7-[[(3,7,11-trimethyl-dodeca-2,6,10-trienyl)-oxy]-methyl]-1,5-benzodioxepine are dissolved in 30 ml of ethyl acetate and hydrogenated under normal conditions in the presence of 300 g of platinum oxide. After the uptake of 3 mol of hydrogen, the hydrogenation is terminated and the catalyst is filtered off. The clear filtrate is evaporated under reduced pressure. The residual 7-[[(3,7,11-trimethyl-dodecyl)-oxy]-methyl]-1,5-benzodioxepine is purified by adsorption on Kieselgel: $n_D^{25} = 1.4968$.

EXAMPLE 22

6 g of 7-[[(3,7,11-trimethyl-dodeca-2,6,10-trienyl)-oxy]-methyl]-1,5-benzodioxepine are suspended in 6 ml of water. The suspension is treated with tetrahydro-furan until a clear solution is obtained. This solution is treated portionwise with stirring at 5°–10° with 2.7 g of N-bromo-succinimide. The resulting mixture is stirred for 1 hour, then treated with 200 ml of water and extracted with diethyl ether. The ether extract is washed with water, dried over sodium sulphate and evaporated under reduced pressure. The residual crude bromohydrin is introduced with stirring into a solution of 1.0 g of sodium in 50 ml of absolute ethanol. The resulting mixture is diluted with 200 ml of water and exhaustively extracted with ether. The ether extract is washed with water, dried over sodium sulphate and evaporated under reduced pressure. The residual 7-[[10,-11-epoxy-3,7,11-trimethyl-dodeca-2,6-dienyl)-oxy]-methyl]-1,5-benzodioxepine is purified by adsorption on Kieselgel: $n_D^{25} = 1.5233$.

EXAMPLE 23

24.8 g of thio-p-cresol are introduced with stirring into a solution of 4.6 g of sodium in 150 ml of absolute ethanol. The resulting mixture is treated dropwise at 30° C with stirring with 57 g of 1-bromo-3,7,11-trimethyl-dodeca-2,6,10-triene. The mixture is then heated under reflux conditions for 2 hours, cooled, poured onto ice and exhaustively extracted with diethyl ether. The ether extract is washed with water, dried over sodium sulphate and evaporated under reduced pressure. The residual 3,7,11-trimethyl-dodeca-2,6,10-trienyl p-tolyl sulphide boils at 145°–150° C/0.05 mmHg.

EXAMPLE 24

In a manner analogous to Example 23;
from thiophenol and 1-bromo-3,7,11-trimethyl-dodeca-2,6,10-triene there is obtained 3,7,11-trimethyl-dodeca-2,6,10-trienyl phenyl sulphide ($n_D^{20} = 1.5428$);
and from 2-thionaphthol and 1-bromo-3,7,11-trimethyl-dodeca-2,6,10-triene there is obtained 3,7,11-trimethyl-dodeca-2,6,10-trienyl 2-naphthyl sulphide ($n_D^{25} = 1.5881$).

EXAMPLE 25

A solution of 10 g of thiophenol in 300 ml of acetone is gradually treated at room temperature with a solution of 4 g of sodium hydroxide in 7 ml of water. 28.5 g of 1-bromo-3,7,11-trimethyl-dodeca-2,6,10-triene are then added dropwise at 0° C. The resulting mixture is stirred at room temperature for 12 hours, diluted with water and freed from acetone under reduced pressure. The aqueous concentrate is exhaustively extracted with diethyl ether. The ether extract is successively washed with 1-N aqueous sodium hydroxide solution and saturated brine, dried over sodium sulphate and evaporated under reduced pressure. The residual 3,7,11-trimethyl-dodeca-2,6,10-trienyl phenyl sulphide is purified by adsorption on aluminum oxide (activity grade III, eluant n - hexane); boiling point = 150° C/0.03 mmHg, $n_D^{20} = 1.5428$.

EXAMPLE 26

16.4 g of 3,7,11 -trimethyl-dodeca-2,6,10-trienyl p-tolyl sulphide are suspended in 15 ml of water. The suspension is treated with tetrahydro-furan until a clear solution is obtained. This solution is treated portionwise with stirring at 0°–5° C with 8.8 g of N-bromo-succinimide. The resulting mixture is stirred for 2 hours, then extracted with 400 ml of diethyl ether. The ether extract is washed with water, dried over sodium sulphate and evaporated under reduced pressure. The residual crude bromo-hydrin is dissolved in 25 ml of absolute ethanol. The resulting solution is added with stirring to a solution of 1.15 g of sodium in 50 ml of absolute ethanol. The mixture obtained is stirred at room temperature for 1 hour, then diluted with water and exhaustively extracted with diethyl ether. The ether extract is washed with water, dried over sodium sulphate and evaporated under reduced pressure. The residual 10,11-epoxy-3,7,11-trimethyl-dodeca-2,6-dienyl p-tolyl sulphide is purified by adsorption on Kieselgel; $n_D^{25} = 1.5411$.

EXAMPLE 27

In the manner given in Example 26;
from 3,7,11-trimethyl-dodeca-2,6,10-trienyl phenyl sulphide there is obtained 10,11-epoxy-3,7,11-trimethyl-dodeca-2,6-dienyl phenyl sulphide ($n_D^{20} = 1.5419$);
and from 3,7,11-trimethyl-dodeca-2,6,10-trienyl 2-naphthyl sulphide there is obtained 10,11-epoxy-3,7,11-trimethyl-dodeca-2,6-dienyl 2-naphthyl sulphide ($n_D^{25} = 1.5444$).

EXAMPLE 28

32.8 g of 3,7,11-trimethyl-dodeca-2,6,10-trienyl p-tolyl sulphide are dissolved in 300 ml of methylene chloride and treated portionwise at 0°–5° C with 18 g of m-chloro-perbenzoic acid. The resulting mixture is further stirred at room temperature for 1 hour, then diluted with 200 ml of methylene chloride. The resulting solution is successively washed with 0.1-N sodium hydroxide solution and water. The methylene chloride phase is separated off, dried over sodium sulphate and evaporated under reduced pressure. The residual 3,7,11-trimethyl-dodeca-2,6,10-trienyl p-tolyl sulphoxide is purified by adsorption on Kieselgel; $n_D^{25} = 1.5414$.

EXAMPLE 29

In a manner analogous to Example 28;
from 3,7,11-trimethyl-dodeca-2,6,10-trienyl phenyl sulphide there is obtained 3,7,11-trimethyl-dodeca-2,6,10-trienyl phenyl sulphoxide ($n_D^{25} = 1.5423$);
and from 3,7,11-trimethyl-dodeca-2,6,10-trienyl 2-naphthyl sulphide there is obtained 3,7,11-trimethyl-dodeca-2,6,10-trienyl 2-naphthyl sulphoxide ($n_D^{25} = 1.5822$).

EXAMPLE 30

6.9 g of 10,11-epoxy-3,7,11-trimethyl-dodeca-2,6-dienyl p-tolyl sulphide are dissolved in 70 ml of methylene chloride. The solution is cooled to 0°–5° C and treated portionwise with stirring with 3.5 g of m-chloroperbenzoic acid. The resulting mixture is stirred at room temperature for 1 hour, then diluted with 50 ml of methylene chloride. The resulting clear solution is successively washed with 0.1-N sodium hydroxide solution and water. The methylene chloride phase is separated off, dried over sodium sulphate and evaporated under reduced pressure. The residual 10,11-epoxy-3,7,11-trimethyl-dodeca-2,6-dienyl p-tolyl sulphoxide is purified by adsorption on Kieselgel; $n_D^{25} = 1.5447$.

EXAMPLE 31

In a manner analogous to Example 30;
from 10,11-epoxy-3,7,11-trimethyl-dodeca-2,6-dienyl phenyl sulphide there is obtained 10,11-epoxy-3,7,11-trimethyl-dodeca-2,6-dienyl phenyl sulphoxide ($n_D^{25} = 1.5430$);

and from 10,11-epoxy-3,7,11-trimethyl-dodeca-2,6-dienyl 2-naphthyl sulphide there is obtained 10,11-epoxy-3,7,11-trimethyl-dodeca-2,6-dienyl 2-naphthyl sulphoxide ($n_D^{25} = 1.5797$).

EXAMPLE 32

A solution of 6.9 g of 10,11-epoxy-3,7,11-trimethyl-dodeca-2,6-dienyl p-tolyl sulphide in 80 ml of methylene chloride is treated portionwise with stirring at 0°–5° C with 7 g of m-chloro-perbenzoic acid. The resulting mixture is stirred at room temperature for 1 hour, then diluted with 80 ml of methylene chloride. The resulting clear solution is successively washed with 0.1-N aqueous sodium hydroxide solution and water. The methylene chloride phase is separated off, dried over sodium sulphate and evaporated under reduced pressure. The residual 10,11-epoxy-3,7,11-trimethyl-dodeca-2,6-dienyl p-tolyl sulphone is purified by adsorption on Kieselgel; $n_D^{25} = 1.5232$.

EXAMPLE 33

In a manner analogous to Example 32;
from 10,11-epoxy-3,7,11-trimethyl-dodeca-2,6-dienyl phenyl sulphide there is obtained 10,11-epoxy-3,7,11-trimethyl-dodeca-2,6-dienyl phenyl sulphone; and from 10,11-epoxy-3,7,11-trimethyl-dodeca-2,6-dienyl 2-naphthyl sulphide there is obtained 10,11-epoxy-3,7,11-trimethyl-dodeca-2,6-dienyl 2-naphthyl sulphone ($n_D^{25} = 1.5908$).

EXAMPLE 34

By the process described in Example 1, 2-bromo-methyl-heptane is reacted with p-hydroxy-benzoic acid methyl ester to produce p-[(1,5-dimethyl-hexyl)-oxy]-benzoic acid methyl ester (boiling point = 132°–133° C/0.1 mmHg; $n_D^{24} = 1,4883$.

EXAMPLE 35

42 g of p-[(1,5-dimethyl-hexyl)-oxy]-benzoic acid methyl ester are dissolved in 250 ml of benzene and treated dropwise with stirring with 50 g of 70% by weight sodium dihydro-bis-(2-methoxy-ethoxy)-aluminate in benzene. The resulting mixture is further stirred at room temperature for 5 hours, then treated with water. The organic phase is separated off, dried over sodium sulphate, carefully filtered (using a filter aid if necessary) and evaporated under reduced pressure. The residual p-[(1,5-dimethyl-hexyl)-oxy]-benzyl alcohol boils at 180°–182° C/1.0 mmHg.

EXAMPLE 36

By the process described in Example 1, p-[(1,5-dimethyl-hexyl)-oxy]-benzyl alcohol is reacted with propyl bromide to give p-[(1,5-dimethyl-hexyl)-oxy]-α-propoxy-toluene (boiling point = 198°–200° C/1.0 mmHg).

EXAMPLE 37

A solution of 23 g. 6,7-epoxy-1-(p-ethylphenoxy)-3,7-dimentyl-2-nonene in 250 ml ethylacetate was trated with 1.0 g PtO₂ and hydrogenated until 2.15 l. of hydrogen (corresponding to 1 double bond) has been taken up. The ethylacetate solution after filtration of Pt was washed with two 100 ml-portions of 2N aqueous NaOH and finally with water. It was dried over magnesium sulfate, filtered and concentrated in vacuo at 35° temperature and 20 mmHg pressure to constant weight; $n_D^{25}$ 1,4965 to produce 6,7-epoxy-1-(p-ethylphenoxy-3,7-dimethylnonane.

EXAMPLE 38

By the procedure of Example 37 starting from: 6,7-epoxy-1-(p-ethylphenoxy)-3-ethyl-7-methyl-2-nonene and H₂ there is produced 6,7-epoxy-1-(p-ethylphenoxy)-3-ethyl-7-methylnonane, $n_D^{24}$ : 1,4971.

EXAMPLE 39

By the procedure of Example 37, 6,7-epoxy-1-(p-ethylphenoxy)-3,7-dimethyl-2-octene is converted to 6,7-epoxy-1-(p-ethylphenoxy)-3,7-dimethyloctane, $n_D^{24}$ : 1,4973.

EXAMPLE 40

By the procedure of Example 37 6,7-epoxy-1-(p-ethylphenoxy)-3,6,7-trimethyl-2-octene is converted to 6,7-epoxy-1-(p-ethylphenoxy)-3,6,7-trimethyl-octane, $n_D^{27}$ : 1,4998.

EXAMPLE 41

Into a flask equipped with a cooling bath, stirrer, thermometer, nitrogen inlet and dropping funnel were placed 122 g of p-ethylphenol and 1.0 l of dimethylformamide. The solution was stirred with 75 g of powdered potassium hydroxide (85%) and the temperature was maintained below 20° C during this addition. It was then cooled and 250 g of 1-bromo-3,7-dimethyl-2,6-octadiene was added dropwise and the reaction was stirred overnight. Thereafter, the solution was poured on a mixture of ice, 2N-NaOH and hexane. The organic layer was then dried over sodium sulfate, filtered and concentrated in vacuo. The product was chromatographed on silicagel using hexane-ethylacetate (9:1 parts by volume) as eluent. The fractions containing p-ethylphenyl-3,7-dimethyl-2,6-octadienyl ether were concentrated in a rotary evaporator. The residue was distilled, b.p. 124°–126°/0.05 mmHg.

EXAMPLE 42

By the procedure of Example 41, 1-bromo-3,7-dimethyl-2,6-nonadiene and p-ethylphenol are reacted to form p-ethylphenyl-3,7-dimethyl-2,6-nonadien-ylether, b.p. 128°–130° C/0.05 mmHg;

1-bromo-3-ethyl-7methyl-2,6-nonadiene and p-ethylphenol are reacted to form p-ethylphenyl-3-ethyl-7-methyl-2,6-nonadienylether, $n_D^{25} = 1,5048$; and 1-bromo-3,6,7-trimethyl-2,6-octadiene and p-ethylphenol are reacted to form p-ethylphenyl-3,6,7-trimethyl-2,6-octadienylether, $n_D^{24} = 1,5141$.

EXAMPLE 43

Into a 2 l flask equipped with a stirrer, thermometer and a cooling bath were placed 30 g of p-ethylphenyl-3,7-dimethyl-2,6-octadienylether and 240 ml of methylenechloride. Nitrogen was bubbled through the system and the stirred mixture was cooled to 0° C. A solution of 22g of m-chloroperbenzoic acid (80%) in 300 ml of methylenechloride was added dropwise over 30 minutes at 0°–5° C. The reaction was stirred 30 minutes longer at 5° C and then the bath was removed to allow the mixture to warm to room temperature. It was stirred at this temperature for 15 minutes and after filtration m-chlorobenzoic acid, the dichloromethane solution was washed successively with two 250 ml portions of 2N aqueous sodium hydroxide, once with 200 ml of 0.1N aqueous sodium-thiosulfate and finally with 250 ml of water. It was dried over magnesium sulfate, filtered and concentrated in vacuo at 35° bath temperature and 20 mmHg pressure to constant weight; $N_D^{20}$ = 1,5025.

EXAMPLE 44

By the procedure of Example 43:

p-ethylphenyl-3-ethyl-7-methyl-2,6-nonadienylether is reacted with m-chloroperbenzoic acid to produce 6,7-epoxy-1-(p-ethylphenoxy)-3-ethyl-7-methyl-2-nonene; $n_D^{23}$ = 1,5026;

p-ethylphenyl-3,7-dimethyl-2,6-nonadienylether is reacted with m-chloroperbenzoic acid, to produce 6,7-epoxy-1-(p-ethylphenoxy)-3,7-dimethyl-2-nonene; $n_D^{20}$ = 1,5097; and p-ethylphenyl-3,6,7-trimethyl-2,6-octadienylether is reacted with m-chloroperbenzoic acid to produce 6,7-epoxy-1-(p-ethylphenoxy)-3,6,7-trimethyl-2-octene; $n_D^{28}$ = 1,5048.

EXAMPLE 45

Preparation of 6,7-Epoxy-1-(1-ethylphenoxy)-3,7-dimethyloctane

In a 1.0 liter four-necked flask fitted with a reflux condenser a mechanical stirrer, dropping funnel and a gas inlet tube is placed 50 ml of dry tetrahydrofurane and 1.5 g NaH (prepared from 50% suspension through washing with tetrahydrofuran). 7.5g of p-ethylphenol in 50 ml of tetrahydrofuran is then added dropwise with stirring while a nitrogen atmosphere is maintained in the flask. The mixture is stirred until solution of NaH is complet, and 13.0 g. 1-bromo-6,7-epoxy-3,7-dimethyloctane in 20 ml hexamethylphosphoric triamide is added dropwise and with stirring. The resulting mixture is boiled under reflux, with stirring for 3 hours. After the addition of 1.0 liter of water the mixture is extracted with 0.5 liters of hexane and hexane extract is dried over sodium sulfate, filtered and concentrated in vacuo with water aspirator. The product was chromatographed on silica gel, fractions eluted with a mixture hexane-ethyl-acetate (9:1 parts by volume) afforded 6,7-Epoxy-1-(1-ethylphenoxy)-3,7-dimethyl-octane $n_D^{24}$ - 1,4973.

EXAMPLE 46

Preparation of 1-Bromo-6,7-epoxy-3,7-dimethyloctane

Into a 2 liter round-bottomed flask equipped with a stirrer, thermometer and cooling bath were placed 20.0 g of 3,7-dimethyl-6-octen-1-bromide and 150 ml dichloromethane. Nitrogen was admitted to the system and the stirred mixture was cooled to 0° C. The solution of 22 g. of m-chloroperbenzoic acid (80%) in 150 ml dichloromethane was added dropwise over 30 minutes at 0° to 5° C. The reaction was stirred over 30 minutes longer at 5° C and then the bath was removed to allow the mixture to warm to room temperature. It was stirred at this temperature for 15 minutes and after filtration of m-chlorobenzoic acid, the dichloromethane solution was washed successively with two 250 ml-portions of 2 N NaOH, once with 200 ml 0.1 N sodium thiosulfate, and finally with 250 ml of water to produce 1-bromo-6,7-epoxy-3,7-dimethyloctane. The product was dried over magnesium sulfate, filtered and concentrated in vacuo at 35° C bath temperature and 20 mmHg pressure to constant weight: $n_D^{20}$ = 1,4986.

EXAMPLE 47

Preparation of P-ethylphenyl-3,7-dimethyl-6-octenyl ether

Into a 2 liter round-bottomed flask equipped with a cooling bath, stirrer and thermometer was placed 70 g. of p-ethylphenol and 400 ml dimethoxy ethane. The resulting solution was stirred and 30 g. of potassium hydroxide in 200 ml ethanol was added within 5 minutes. The temperature was maintained below 20° C during this addition and then 110 g. of 1-bromo-3,7-dimethyl-6-octene was added dropwise over 15 minutes. The reaction was stirred for two hours longer at 80° C and then allowed to rise to room temperature. After 3 hours the reaction was poured into a mixture of 500 g. of ice and 1 liter of hexane. The phases were separated and the aqueous layer was reextracted with two 0.5 l-portions hexane. All organic phases were combined and washed successively with 1.0 liter of water, two 250 ml portions of 2N sodium hydroxide and 1.0 liter of water. The organic layer was then dried over sodium sulfate, filtered, and concentrated in vacuo with water aspirator. The dark solution was chromatographed on 1 kg silica gel in hexane-ethylacetate (9:1 parts by volume). The fractions yielding p-ethyphenyl-3,7-dimethyl-6-octenyl ether were concentrated in a rotary evaporator at 40° C bath temperature using a water pump for the vacuum. The residue was distilled through a small Widmer column. The fraction of b.p. 118°–120° C 0.05 mmHg was p-ethylphenyl-3,7-dimethyl-6-octenyl ether.

EXAMPLE 48

49 g of dry diethylamine are dissolved in 530 ml of anhydrous ether and mixed at −10° C with stirring with 420 ml of a 15% by weight solution of butyl-lithium in hexane. The mixture is stirred at room temperature for 1 hour. 10 ml of the 1-molar solution of diethylamine-lithium thus obtained are treated with a solution of 3 g of p-[(1,5-dimethyl-hexyl)-oxy]benzoic acid methyl ester (see Example 34) in 30 ml of diethyl ether. The resulting mixture is stirred at room temperature for 4 hours, then washed with 0.1-N aqueous hydrochloric acid and with water, dried over sodium sulphate and evaporated under reduced pressure. The residual p-[(1,5-dimethyl-hexyl)oxy]-N,N-diethyl-benzamide is purified by adsorption on Kieselgel; boiling point = 205°–208° C/0.1mmHg.

EXAMPLE 49

By the procedure given in Example 47, diisobutylamine is reacted with p-[(1,5-dimethyl-hexyl)-oxy]-benzoic acid methyl ester to produce p-[(1,5-dimethyl-hexyl)-oxy]-N,N-diisobutylbenzamide ($n_D^{24}$ = 1.4968).

EXAMPLE 50

By the procedure described in Example 1, 2-bromo-6-methylheptane is reacted with vanillic acid methyl ester to produce 4-[(1,5-dimethyl-hexyl)-oxy]-m-methoxy-benzoic acid methyl ester (boiling point = 198°–200° C/0.1 mmHg).

EXAMPLE 51

By the procedure described in Example 48, dimethylamine is reacted with 4-[(1,5-dimethyl-hexyl)-oxy]-m-methoxy-benzoic acid methyl ester to produce 4-[(1,5- dimethyl-hexyl)-oxy]-m-methoxy-N,N-diethyl-benzamide (boiling point = 180°–182° C/0.1 mmHg).

EXAMPLES 52 to 55

In Examples 52 to 55 hereinafter, which relate to tests demonstrating the activity of the phenyl derivatives provided by the invention, the various phenyl derivatives are referred to by way of the letters indicated in the following list:

A) 2,4-dichloro-phenyl 6,7-epoxy-3,7-dimethyl-oct-2-enyl ether
B) 3,7-dimethyl-octa-2,6-dienyl benzyl sulphide
C) 3,7-dimethyl-octa-2,6-dienyl p-tolyl sulphoxide
D) 1,5-dimethyl-hexyl p-tolyl sulphoxide
E) p-[(1,5-dimethyl-hexyl)-oxy]-benzaldehyde
F) p-[(1,5-dimethyl-hexyl)-oxy]-acetophenone
G) 1-benzyloxy-6,7-epoxy-3,7-dimethyl-oct-2-ene
H) 6-[[(6,7-epoxy-3,7-dimethyl-oct-2-enyl)-oxy]-methyl]=1,4-benzodioxan
J) 3,7-dimethyl-octa-2,6-dienyl p-tolyl sulphide
K) 3,7-dimethyl-octa-2,6dienyl o-tolyl sulphide
L) 6,7-epoxy-3,7-dimethyl-oct-2-enyl p-tolyl sulphide
M) 6,7-epoxy-3,7-dimethyl-oct-2-enyl o-tolyl sulphide
N) 3,7-dimethyl-octa-2,6-dienyl phenyl sulphoxide
O) 6,7-epoxy-3,7-dimethyl-oct-2-enyl p-tolyl sulphoxide
P) p-[(1,5-dimethyl-hexyl)-oxy]-benzyl alcohol
Q) 10,11-epoxy-3,7,11-trimethyl-dodeca-2,6-dienyl p-tolyl sulphone
R) 10,11-epoxy-3,7,11-trimethyl-doeca-2,6-dienyl 2-naphthyl sulphone.

EXAMPLE 52

Two filter-paper discs (24 cm$^2$) are sprayed with a solution of active substance in acetone. After drying, they are so fixed together that a tunnel is formed to shelter larvae of the cockroach (*Blatella germanica*) in the final larval stage. The same is done with an untreated filer-paper disc and a filter-paper disc treated only with acetone. The larvae remain in continuous contact with the filter paper and are provided with water and food. The further development of the larvae is noted daily and the results are evaluated (100% disturbance of metamophosis; a normal adult develops from none of the larvae).

Results

| Active substance | Amount of active substance (g/cm$^2$) | No. of larvae | No. of normal imagos | Activity (%) |
| --- | --- | --- | --- | --- |
| Q | 10$^{-4}$ | 10 | 1 | 90 |
| R | 10$^{-4}$ | 10 | 0 | 100 |
| Control with acetone | — | 10 | 10 | 0 |
| Control without acetone | — | 10 | 10 | 0 |

EXAMPLE 53

A cotton disc (10 cm$^2$) is sprayed with a solution of active substance in acetone. After drying, 30-60 freshly laid eggs of the meal moth (*Ephestia Kuhniella*) are placed on the disc. The same is done with an untreated cotton disc and a cotton disc sprayed only with acetone. The discs are placed in a cage and kept at 25° C and 90% relative humidity. The development of the eggs is registered over a period of a few days and the results are evaluated (100% egg mortality: no development of the embryos in the eggs laid on discs soaked with active substance).

Results

| Active substance | Amount of active substance g/cm$^2$ | No. of eggs | No. of larvae | Mortality (%) |
| --- | --- | --- | --- | --- |
| A | 10$^{-4}$ | 37 | 0 | 100 |
|   | 10$^{-5}$ | 40 | 1 | 98 |
| B | 10$^{-4}$ | 40 | 3 | 92 |
|   | 10$^{-5}$ | 41 | 0 | 100 |
| C | 10$^{-4}$ | 39 | 0 | 100 |
|   | 10$^{-5}$ | 47 | 0 | 100 |
| D | 10$^{-4}$ | 37 | 0 | 100 |
|   | 10$^{-5}$ | 36 | 0 | 100 |
|   | 10$^{-6}$ | 42 | 36 | 14 |
| E | 10$^{-4}$ | 36 | 0 | 100 |
|   | 10$^{-5}$ | 57 | 0 | 100 |
|   | 10$^{-6}$ | 32 | 1 | 97 |
| F | 10$^{-4}$ | 49 | 0 | 100 |
|   | 10$^{-5}$ | 33 | 0 | 100 |
|   | 10$^{-6}$ | 36 | 6 | 80 |
| G | 10$^{-4}$ | 80 | 0 | 100 |
|   | 10$^{-5}$ | 92 | 13 | 83 |
| H | 10$^{-4}$ | 41 | 4 | 90 |
|   | 10$^{-5}$ | 42 | 11 | 74 |
| L | 10$^{-4}$ | 44 | 0 | 100 |
|   | 10$^{-5}$ | 60 | 0 | 100 |
| M | 10$^{-4}$ | 63 | 0 | 100 |
|   | 10$^{-5}$ | 50 | 23 | 54 |
| N | 10$^{-4}$ | 83 | 0 | 100 |
| O | 10$^{-4}$ | 42 | 4 | 90 |
| P | 10$^{-4}$ | 32 | 0 | 100 |
|   | 10$^{-5}$ | 35 | 0 | 100 |
|   | 10$^{-6}$ | 32 | 27 | 15 |
| Control with acetone | — | 50 | 50 | 0 |
| Control without acetone | — | 49 | 46 | 6 |

EXAMPLE 54

A disc of woolen material (10 cm$^2$) is sprayed with a solution of active substance in acetone and, together with an untreated disc and a disc treated only with acetone, hung in a cage occupied by 20 young clothes moths (*Tineola biselliela*). The development of eggs laid at 25° C is noted over a period of 4 days and the results are evaluated (100% sterilant activity: larvae hatch from none of the eggs laid on treated and untreated discs of woolen material; 100% ovicidal activity: larvae hatch from none of the eggs laid on treated discs of woolen material).

Results

| Active substance | Amount of active substance (g/cm$^2$) | Sterilant activity (%) | Ovicidal activity (%) |
| --- | --- | --- | --- |
| H | 10$^{-3}$ | 9 | 93 |
| J | 10$^{-3}$ | 0 | 100 |
| K | 10$^{-3}$ | 0 | 82 |
| Control with acetone | — | 0 | 0 |
| Control without acetone | — | 0 | 0 |

EXAMPLE 55

A filter-paper strip (90 cm$^2$) is sprayed with a solution of active substance in acetone. After drying, 3–4 pairs of freshly moulted imagos of the cotton bug (*Dystercus cingulatus*) are placed on the strip. The same is done with an untreated filter-paper strip and a filter-paper strip treated only with acetone. The development of the eggs laid daily is noted and the results are evaluated (100% egg-mortality: no development of the embryos in the eggs laid on filter-paper strips soaked with active substance).

Results

| Active substance | Amount of active substance (g/cm$^2$) | No. of eggs | No. of larvae | Egg Mortality (%) |
|---|---|---|---|---|
| D | 10$^{-5}$ | 59 | 0 | 100 |
| E | 10$^{-5}$ | Mortality of the imago | | |
| P | 10$^{-5}$ | 190 | 1 | 99 |
| Control with acetone | — | 270 | 262 | 3 |
| Control without | | 410 | | |

| Active substance | Amount of active substance (g/cm$^2$) | No. of eggs | No. of larvae | Egg Mortality (%) |
|---|---|---|---|---|
| acetone | — | | 390 | 5 |

We claim:

1. A compound of the formula:

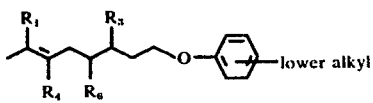

wherein R$_1$ is methyl or ethyl, R$_2$ and R$_3$ are hydrogen, methyl or ethyl; R$_4$ is hydrogen or methyl; R$_5$ and R$_6$ are hydrogen or lower alkyl; Y$_1$ is lower alkyl; and m and n are 0 or 1.

2. The compound of claim 1 wherein said compound has the formula:

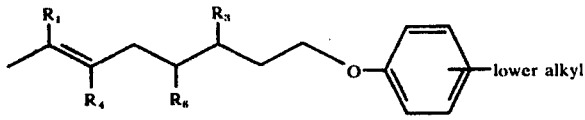

wherein R$_1$, R$_3$, R$_4$, R$_6$ and Y are as above.

3. The compound of claim 1 wherein said compound is p-ethylphenyl-3,7-dimethyl-6-octenyl ether.

* * * * *

UNITED STATES PATENT AND TRADEMARK OFFICE
CERTIFICATE OF CORRECTION

PATENT NO. : 4,001,339
DATED : Jan. 4, 1977
INVENTOR(S) : Madhukar Subraya Chodnekar et al.

It is certified that error appears in the above-identified patent and that said Letters Patent are hereby corrected as shown below:

Column 30, Claim 1, delete the formula and insert:

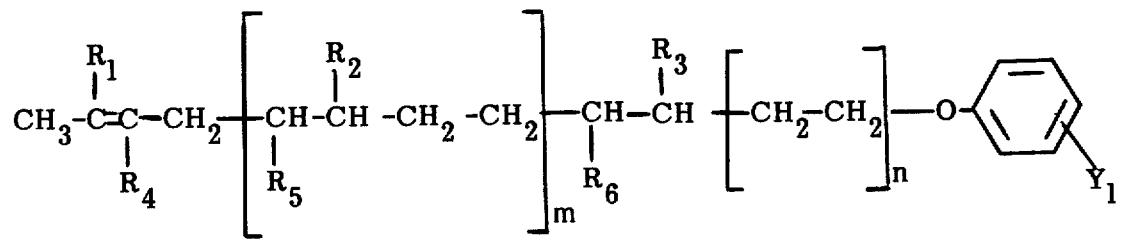

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*